United States Patent [19]

Imonti

[11] Patent Number: 5,178,605

[45] Date of Patent: Jan. 12, 1993

[54] COAXIAL FLOW IRRIGATING AND ASPIRATING ULTRASONIC HANDPIECE

[75] Inventor: Maurice M. Imonti, San Juan Capistrano, Calif.

[73] Assignee: Alcon Surgical, Inc., Fort Worth, Tex.

[21] Appl. No.: 764,036

[22] Filed: Sep. 23, 1991

[51] Int. Cl.$^5$ ............................................. A61B 17/20
[52] U.S. Cl. ................................... 604/22; 128/24 AA
[58] Field of Search ................. 604/22; 606/169–171; 128/24 AA

[56] References Cited

U.S. PATENT DOCUMENTS

| | | | |
|---|---|---|---|
| 3,645,255 | 2/1972 | Robinson | 128/24 AA |
| 3,809,093 | 5/1974 | Abraham . | |
| 4,316,465 | 2/1982 | Dotson, Jr. . | |
| 4,526,571 | 7/1985 | Wuchinich | 128/24 AA |
| 4,577,629 | 3/1986 | Martinez . | |
| 4,609,368 | 9/1986 | Dotson, Jr. | 604/22 |
| 4,747,820 | 5/1988 | Hornlein et al. | 604/22 |
| 4,753,234 | 6/1988 | Martinez . | |
| 4,804,364 | 2/1989 | Dieras et al. . | |
| 4,808,154 | 2/1989 | Freeman | 604/22 |
| 4,861,332 | 8/1989 | Parisi . | |
| 4,867,141 | 9/1989 | Nakada et al. | 128/24 AA |
| 4,904,238 | 2/1990 | Williams . | |
| 4,922,903 | 5/1990 | Welch et al. | 604/22 |
| 4,931,047 | 6/1990 | Broadwin et al. | 604/22 |
| 4,989,588 | 2/1991 | Kubota et al. | 604/22 |
| 5,015,227 | 5/1991 | Broadwin et al. | 604/22 |
| 5,038,756 | 8/1991 | Kepley | 128/24 AA |

Primary Examiner—Stephen C. Pellegrino
Assistant Examiner—Michael Rafa
Attorney, Agent, or Firm—Jeffrey S. Schira

[57] ABSTRACT

A coaxial flow irrigation and aspiration ultrasonic handpiece for use in surgical operations includes the combination of an elongated outer shell, inner shell and ultrasonic horn assembly disposed within the inner shell. A sealing end cap is provided which functions to center the inner shell within the outer shell as well as to form an irrigation channel therebetween for supplying irrigation fluid to the distal end tip of the surgical handpiece. The sealing end cap includes an irrigation channel and electrical cable integrally therewith to facilitate ease of assembly of the handpiece as well as connection with sources of irrigation fluid and means for providing aspiration.

5 Claims, 3 Drawing Sheets

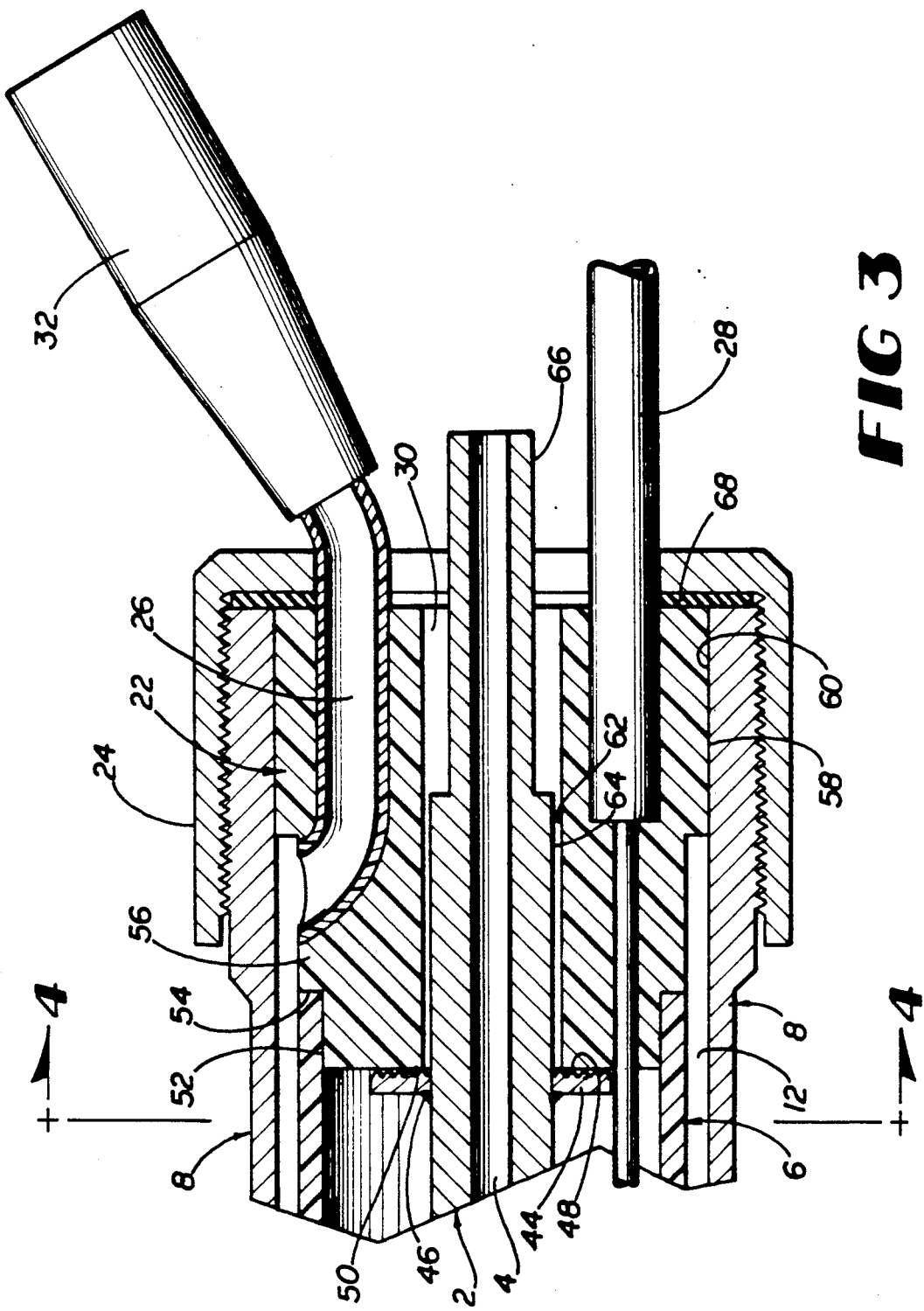

COAXIAL FLOW IRRIGATING AND ASPIRATING ULTRASONIC HANDPIECE

FIELD OF THE INVENTION

The invention relates to a coaxial flow irrigating and aspirating ultrasonic surgical handpiece which is particularly effective in ophthalmic surgery. The ultrasonic surgical handpiece includes the combination of an inner and outer sleeve together with a sealing cap which, in one aspect, permit influx of irrigation fluid via the proximal end of the handpiece to provide a more easily manipulated surgical tool.

BACKGROUND ART

In the prior art, a plurality of hand-held devices have been proposed for removal of body tissue during surgical procedures. One particular surgical device includes an ultrasonically driven surgical tool which includes both irrigation fluid supply as well as a source of vacuum for aspiration. Typically, these devices have the irrigation fluid supply tube configured in close proximity to the surgical tip assembly, thereby interfering with easy maneuvering of the handpiece during surgery. U.S. Pat. Nos. 4,753,234 to Martinez and 4,861,332 to Parisi show surgical cutting instruments having these types of irrigation fluid tube configurations.

Other prior art devices have been proposed wherein the surgical handpieces include a proximal end cap which introduces or provides access therethrough for means to operate the surgical handpiece. U.S. Pat. No. 4,577,629 to Martinez discloses a surgical cutting instrument for use in ophthalmic surgery which includes a rear plug. The rear plug has a first bore to permit aspiration of cut material and a second bore for supplying air pressure to the cutting mechanism within the instrument. U.S. Pat. No. 4,316,465 to Dotson, Jr. discloses an ophthalmic handpiece which includes a needle having coaxially irrigation and aspiration passageways. The handpiece also includes a rear plug having tubing connectors therein for connection with an irrigation fluid source and a source of aspiration or vacuum. Neither of these patents disclosing surgical cutting instruments having end caps or plugs therewith teach or fairly suggest all of the features of the present invention including an ultrasonic handpiece having an inner and outer shell and sealing end cap therewith.

U.S. Pat. No. 4,804,364 to Dieras et al. discloses another ultrasound apparatus intended for the curettage of biological tissue using ultrasonic vibrations. In this device, and in an effort to improve upon prior art devices that include suction and irrigation conduits which greatly exaggerate the diameter of a surgical handpiece, a connector block is provided at the proximal end of the handpiece which includes an irrigation tube therethrough as well as a connector connected to a source of vacuum.

However, a need has developed to provide improved ultrasonic handpieces which are uniformly sized to permit ease of handling, include features that facilitate assembly or disassembly of the handpiece, provide separation between electronics and fluids and simplify the overall surgical handpiece design.

In response to this need, an ultrasonic surgical handpiece has been developed which includes a outer shell, inner shell, an ultrasound horn assembly within the inner shell and a sealing end cap to facilitate connection to a source of irrigation fluid, electrical power and a source of aspiration.

None of the prior art mentioned above teaches or fairly suggest all of the features of the present invention including the combination of inner and outer shells, ultrasound horn assembly and sealing end cap.

SUMMARY OF THE INVENTION

It is accordingly an object of the present invention to provide an ultrasonic surgical handpiece having coaxial flow paths for irrigation fluids and aspirated body tissue or other material.

It is a further object of the present invention to provide an ultrasonic handpiece having a uniform and slim design to permit ease of manipulation during surgical procedures.

It is a still further object of the present invention to provide an ultrasonic handpiece which provides separation between fluids passing therethrough and electrical components to reduce or eliminate the possibility of electrical short circuiting.

It is a further object of the present invention to provide an ultrasonic handpiece which includes an inner and outer shell and sealing means which eliminate internal tubing as well as provide for ease of assembly and disassembly of the handpiece.

In satisfaction of the foregoing objects and advantages, there is provided an ultrasonic handpiece assembly having coaxial flow paths for irrigation and aspiration which includes the combination of an outer shell, inner shell, ultrasonic horn assembly and sealing end cap. The inner shell and sealing end cap are designed to engage the inner surface of the outer shell to create an irrigation flow path as well as separate irrigating fluids from the electrical components of the ultrasonic horn assembly. The sealing end cap also facilitates ease of assembly by centering the inner shell within the outer shell as well as preventing leakage of irrigation fluid outside the handpiece. In a further embodiment, the sealing means cooperate with the ultrasonic horn assembly to prevent rotation thereof during use of the surgical handpiece.

BRIEF DESCRIPTION OF DRAWINGS

Reference is now made to the drawings accompanying the application wherein:

FIG. 3 shows a cross-sectional view of the proximal end of the handpiece depicted in FIG. 1 enlarged to show greater detail.

DESCRIPTION OF THE PREFERRED EMBODIMENTS

The present invention is concerned with an improved coaxial flow irrigation and aspiration ultrasonic handpiece that may be used in surgical procedures such as ophthalmic surgery. According to the present invention, it has been discovered that the risk of electrical short circuiting may be reduced or eliminated by the novel combination of an outer shell, inner shell, ultrasound horn assembly and sealing end cap which provide separation between the electrical components of the horn assembly and irrigating fluid flowing therethrough. The ultrasonic handpiece of the present invention also provides a slim and more easily maneuverable design by including means in the sealing end cap for transmission of irrigation fluid, flow of aspirated materials and electrical conductors. In addition, the combination of the inner and outer sleeves provides a handpiece design which is easily assembled or disassembled by removal of the sealing end cap and achieves coaxially flow of irrigants and aspirants with a minimum number of apparatus elements. No special tubing or other connectors, as are included in other prior art devices, are necessary in the design of the inventive ultrasonic surgical handpiece.

Figure 1:
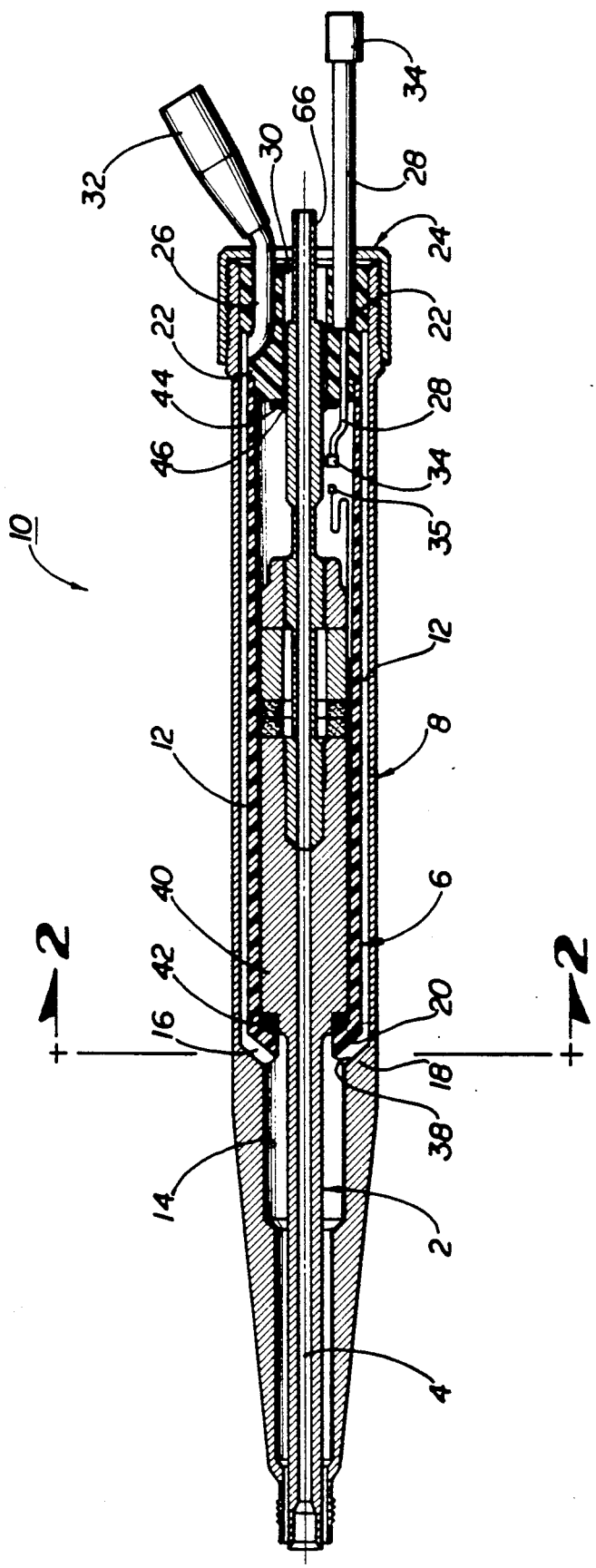
FIG. 1 is a side view partly in cross-section of the ultrasonic surgical handpiece of the present invention.

With reference to FIG. 1, a first embodiment of the inventive coaxial flow ultrasonic surgical handpiece is designated by the reference numeral 10 and seen to include an ultrasonic horn assembly 2 having an aspiration port 4 therethrough, an elongated tubular inner shell 6 and an elongated tubular outer shell 8. The inner shell 6 is disposed within the outer shell 8 so as to form an irrigation channel 12 therebetween. The irrigation channel 12 communicates with the annulus 14 which surrounds the ultrasonic horn assembly 2 via the passageway 16 which is configured between the shoulder 18 of the outer shell 8 and the shoulder 20 of the inner shell 6. The manner in which the irrigation channel 12 and annulus 14 interconnect as well as the engagement of the shoulder 18 of the outer shell 8 with the shoulder 20 of the inner shell 6 will be described in greater detail hereinafter. By axially aligning the inner shell 6 with the outer shell 8, a coaxial flow relationship is formed between the aspiration port 4 and the annulus 14 and irrigation channel 12.

It should be understood that any known ultrasonic horn assembly having an aspiration port therethrough and capable of transmitting vibrations along the distal end thereof for surgical procedures may be utilized in the invention ultrasonic surgical handpiece. Since these types of vibratory cutting instruments are well known in the art, the ultrasonic horn assembly is not considered an aspect of the present invention, and therefor, a further specific description of the individual components thereof is not deemed necessary.

The proximal end of the ultrasonic handpiece 10 includes a sealing end cap 22 which engages the proximal end portions of the inner shell 6 and outer shell 8. The sealing end cap 22 is further secured in place by the combination of a slip washer 68 and a compression nut 24 which is designed to threadably engage the outer shell 8. The sealing end cap 22 is configured to provide access therethrough for irrigation fluid, flow of aspirants and conduction of electrical power to the ultrasonic horn assembly. Specifically, the sealing end cap 22 includes irrigation tubing 26 therethrough, a port 30 for permitting passage of the proximal end of the ultrasonic horn assembly therethrough and an electrical cable 28 to provide electrical power to the ultrasonic horn assembly electrical components. In this manner, entry and exit of all fluids and electrical power are located at the proximal end of the ultrasonic handpiece 10 to provide a uniform and slim design to facilitate ease of use during surgery.

In the preferred embodiment, the irrigation tube 26 includes a coupling portion 32 at the proximal end thereof and is integrally molded in place in the sealing end cap 22. In addition, the electrical cable 28 is molded in the sealing end cap 22 and includes electrical connectors 34 at the ends thereof to facilitate connection between a power source and the ultrasonic horn assembly electrical connector 35. By providing a sufficient amount of electrical conductor between the ultrasonic horn assembly and the sealing end cap disposed within the inner shell, an electrical connection may be made prior to engaging the sealing end cap 22 onto the distal end of the surgical handpiece 10. Of course, other means of providing electrical interconnection between a power source (not shown) and the ultrasonic horn assembly may be utilized.

Figure 2:
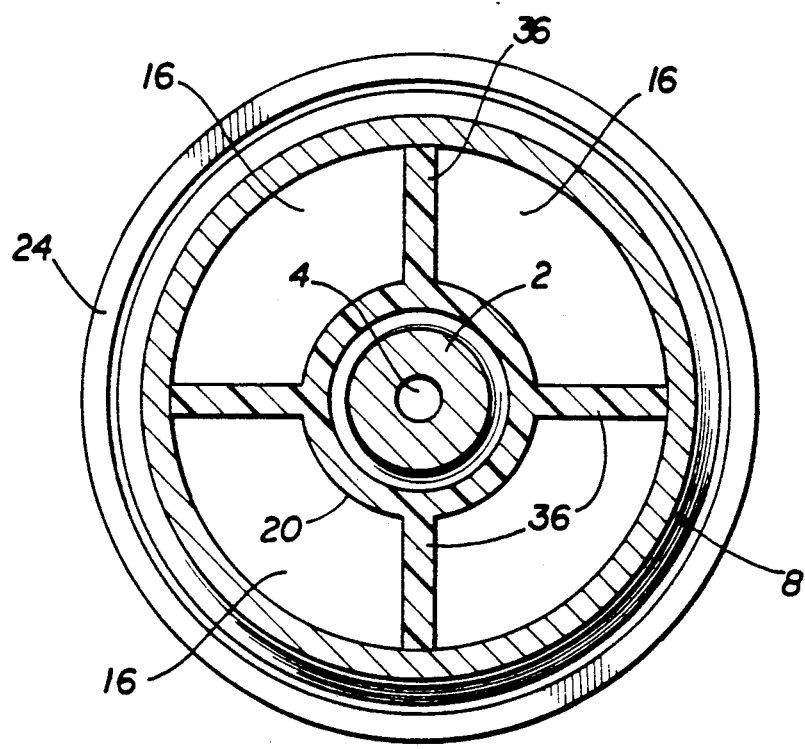
FIG. 2 is an enlarged cross-sectional view taken along lines 2—2 in FIG. 1.

With reference now to FIGS. 1 and 2, the manner in which the inner shell 6 engages the outer shell will now be described. The shoulder 20 of the inner shell 6 includes a plurality of vanes 36 extending outwardly therefrom. The vanes 36 are designed to seat against the face 38 of the shoulder 18 of the outer shell 8. The shoulder 18 is angled towards the distal end of the handpiece 10 to further center the inner shell 6 within the outer shell 8. Although vanes 36 are depicted in combination with the shoulder 20, other means of providing a passageway interconnecting the irrigation channel 12 and annulus 14 may be utilized. One example of an alternative configuration would be to have the shoulder 20 directly seat against the face 38 of the shoulder 18. In this configuration, ports may be included through the shoulder 20 to interconnect the irrigation channel 12 and annulus 14.

With reference to FIG. 1 again, the shoulder 20 cooperates with the stepped portion 40 of the horn assembly 2 and an O-ring 42 to create a seal between the interior of the inner shell 6 and the annulus 14. As will be described in more detail later, compression of the sealing end cap 22 by the compression nut 24 forces the ultrasonic horn assembly 2 towards the distal end of the handpiece 10 which provides a seal by compression of the O-ring 42 between the shoulder 20 and step portion 40 of the ultrasonic horn assembly 2.

With reference to FIG. 3, the proximal end of the handpiece 10 is shown enlarged and with parts in cross-section to show greater detail concerning the sealing end cap 22 and its intended function. The ultrasonic horn assembly 2 includes a washer 44 which may be, for example, attached to the ultrasonic horn assembly by soldering at reference numeral 46. The washer 44 includes a barbed face 48 which is designed to engage the opposing face 50 of the sealing end cap 22. Upon compression of the sealing end cap 22 by the compression nut 24, the barbed face 48 of the washer 44 engages the face 50 of the sealing end cap 22 to prevent rotation of the ultrasonic horn assembly during use.

The sealing end cap 22 is configured in such a manner as to provide a plurality of sealing areas to prevent leakage of irrigation fluid into the inner chamber of inner shell 6 or leakage past the outer shell 8 and compression nut 24. A first sealing area includes the face 52 of the sealing end cap 22 engaging the inner surface of the proximal end of the inner shell 6. In cooperation with this first sealing area, a second sealing area is provided by the face 54 on the stepped portion 56 of the sealing end cap 22 which is designed to engage the proximal end face of the inner shell 6. These two sealing areas effectively prevent influx of irrigation fluid within the chamber housing the ultrasonic horn assembly and electrical components therewith.

The sealing end cap also provides a sealing area for the outer shell 8 by engagement of the face 58 of the sealing end cap 22 and the inner surface 60 of the proximal end of the outer shell 8. Another sealing area is indicated by engagement of the inner surface of the bore 62 in the sealing end cap 22 and the outer surface 64 of the proximal end of the ultrasonic horn assembly 2. The ultrasonic horn assembly 2 may include a reduced diameter proximal end portion 66 to facilitate attachment to a source of vacuum via tubing or the like.

Figure 4:
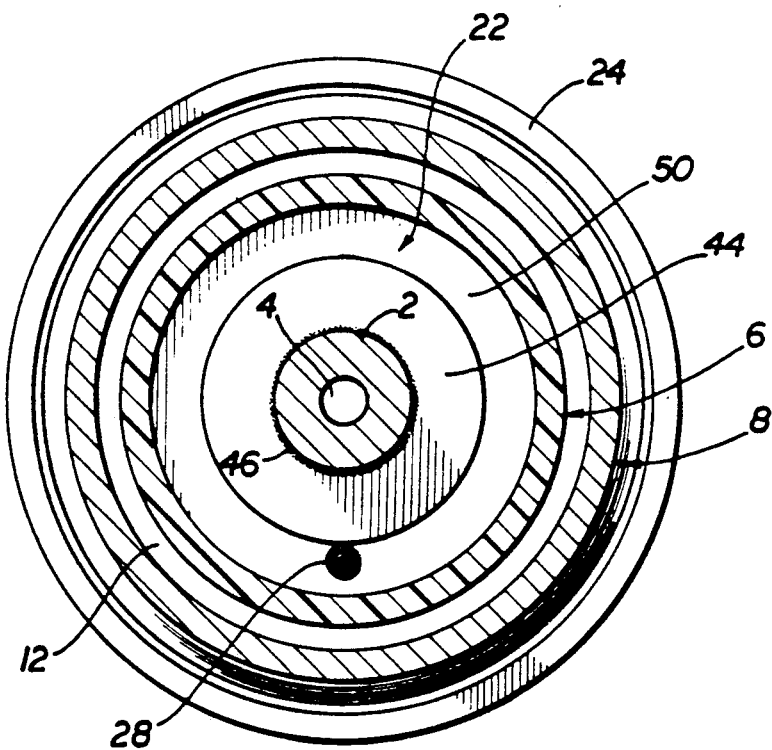
FIG. 4 shows a cross-sectional view taken along lines 4—4 in FIG. 3.

With reference to FIG. 4, a cross-sectional view along the line 4—4 more clearly depicted the manner in which the inner shell 6 is centered within the outer shell 8. As can be seen from FIG. 4, the inner shell 6 and outer shell 8 create the annular irrigation channel 12 which permits flow of irrigating fluid to the distal end tip of the ultrasonic handpiece 10.

When assembling the ultrasonic handpiece, the ultrasonic horn assembly and inner shell are disposed within the outer shell 8 such that the shoulder 20 of the inner shell 6 engages the shoulder 18 of the outer shell 8. In addition, the O-ring 42 engages the inner face shoulder 20 of the inner shell 6. Once the ultrasonic horn assembly is in place, an electrical connection may be made between the source of electrical power (not shown) via electrical conductor 28 and the electrical components of the ultrasonic horn assembly 2. Once the electrical connection is made, the sealing end cap is placed into the outer shell 8 and pushed against the inner shell 6. The stepped configuration of the sealing end cap 22 permits contact between the sealing end cap 22 and the inner surface of the inner shell as well as the proximal end face thereof. By this configuration, the inner shell is axially aligned with the outer shell 8 and the ultrasonic horn assembly 2. The length of the stepped portion 56 of the sealing end cap 22 is longer than the distance between the proximal end face of the inner shell 6 and the proximal end face of the outer shell 8. with this configuration, threading of the compression nut 24 and slip washer 68 compresses the sealing end cap 22 and causes the cap 22 to bell outwardly and push down against the inner shell causing the ultrasonic horn assembly and O-ring 42 to seal itself against the inner shell. In addition, this expansion and pushing of the sealing end cap 22 provides sealing between the interior of the inner shell 6 and the irrigation channel 12 and between the irrigation channel 12 and the exterior of the surgical handpiece. Furthermore, compression of the sealing end cap 22 causes the seal to embed itself against the barbed surface 48 of the washer 44 to prevent rotation of the horn assembly 2 during use.

The sealing end cap may be made out of any material having sufficient flexibility to provide sealing against surfaces of the inner and outer shell. A preferred material would include silicon. A preferred material for the inner shell would include plastic to further minimize the possibility of electrical short circuiting. A preferred material for the outer shell would include a metallic material.

As such, an invention has been disclosed in terms of preferred embodiments thereof which fulfill each and every one of the objects of the invention as set forth hereinabove and provides a new and improved coaxially flow irrigation and aspiration ultrasonic surgical handpiece.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:
1. An ultrasonic surgical handpiece, comprising:
 a) an outer shell having a hollow interior and a length;
 b) an inner shell having a hollow interior telescopically received in the hollow interior of the outer shell;
 c) a means for centering the inner shell within the outer shall so as to define an irrigation channel between the outer shell and the inner shell along the length of the outer shell;
 d) an ultrasonic horn assembly having a longitudinal aspiration port telescopically received in the hollow interior of the inner shell; and
 e) a means for fluid-tight sealing of the horn assembly within the inner shell and for fluid-tight sealing of the inner shell within the outer shell.

2. The handpiece of claim 1 wherein the means for fluid-tight sealing of the horn assembly within the inner shell and for fluid-tight sealing of the inner shell within the outer shell further comprises a means for coupling a source of irrigation fluid to the irrigation channel.

3. The handpiece of claim 1 wherein the means for fluid-tight sealing of the horn assembly within the inner shell and for fluid-tight sealing of the inner shell within the outer shell further comprises a means for coupling a source of electrical power to the horn assembly.

4. The handpiece of claim 1 wherein the means for fluid-tight sealing of the horn assembly within the inner shell and for fluid-tight sealing of the inner shell within the outer shell further comprises a means for permitting the coupling of a source of vacuum to the aspiration port in the horn assembly.

5. An ultrasonic surgical handpiece, comprising:
 a) an outer shell having a hollow interior and a length;
 b) an inner shell having a hollow interior telescopically received in the hollow interior of the outer shell;
 c) a means for centering the inner shell within the outer shall so as to define an irrigation channel between the outer shell and the inner shell along the length of the outer shell;
 d) an ultrasonic horn assembly having a longitudinal aspiration port telescopically received in the hollow interior of the inner shell; and
 e) a means for fluid-tight sealing of the horn assembly within the inner shell and for fluid-tight sealing of the inner shell within the outer shell having
  i) a means for coupling a source of irrigation fluid to the irrigation channel,
  ii) a means for coupling a source of electrical power to the horn assembly and
  ii) a means for permitting the coupling of a source of vacuum to the aspiration port in the horn assembly.

* * * * *

UNITED STATES PATENT AND TRADEMARK OFFICE
CERTIFICATE OF CORRECTION

PATENT NO. : 5,178,605

DATED : January 12, 1993

INVENTOR(S) : Imonti

It is certified that error appears in the above-identified patent and that said Letters Patent is hereby corrected as shown below:

COLUMN 1, Line 66, delete "a outer" substitute --an outer--.

COLUMN 2, Line 66, delete "sound horn" substitute --sonic horn--

COLUMN 6, Line 47, delete "outer shall" substitute -- outer shell--.

Signed and Sealed this

Sixteenth Day of November, 1993

*Attest:*

BRUCE LEHMAN

*Attesting Officer*     *Commissioner of Patents and Trademarks*